(12) United States Patent
Lai et al.

(10) Patent No.: US 9,140,725 B2
(45) Date of Patent: Sep. 22, 2015

(54) RESISTIVITY-MEASURING DEVICE

(71) Applicant: TPK TOUCH SOLUTIONS (XIAMEN) INC., Xiamen (CN)

(72) Inventors: Yankun Lai, Zhangzhou (CN); Lewei Yu, Xiamen (CN); Minxuan Li, Longyan (CN)

(73) Assignee: Optera Technology (Xiamen) Co., Ltd., Xiamen (CN)

( * ) Notice: Subject to any disclaimer, the term of this patent is extended or adjusted under 35 U.S.C. 154(b) by 147 days.

(21) Appl. No.: 13/898,492

(22) Filed: May 21, 2013

(65) Prior Publication Data

US 2013/0314112 A1 Nov. 28, 2013

(30) Foreign Application Priority Data

May 24, 2012 (CN) .......................... 2012 1 0171113

(51) Int. Cl.
 *G01R 31/00* (2006.01)
 *G01R 1/073* (2006.01)
 *G01R 31/01* (2006.01)
 G01N 27/04 (2006.01)
 G01R 27/14 (2006.01)

(52) U.S. Cl.
 CPC ............ *G01R 1/07307* (2013.01); *G01R 31/01* (2013.01); *G01N 27/04* (2013.01); *G01R 27/14* (2013.01)

(58) Field of Classification Search
 CPC ..... G01R 1/07307; G01R 27/14; G01N 24/04
 USPC .................. 324/750.01, 500, 750.05, 750.13, 324/750.2–750.26; 356/3.01–3.15, 356/139.01–139.1
 See application file for complete search history.

(56) References Cited

U.S. PATENT DOCUMENTS

| 4,657,372 | A | * | 4/1987 | Ikeda et al. ...................... 399/13 |
| 5,055,779 | A | * | 10/1991 | Kerschner et al. ....... 324/757.02 |
| 6,651,014 | B2 | | 11/2003 | Chandra et al. |

FOREIGN PATENT DOCUMENTS

TW                M399990 U1    3/2011

* cited by examiner

*Primary Examiner* — Melissa Koval
*Assistant Examiner* — Trung Nguyen
(74) *Attorney, Agent, or Firm* — Gokalp Bayramoglu (57) ABSTRACT

A resistivity-measuring device comprising: a carrier platform used for loading a plurality of products under measure; a material-incoming conveyor, on which the carrier platform is disposed, and comprising a material-incoming guide wheel group for moving the carrier platform horizontally; a probe module, used for measuring the resistance of the products under measure; a probe position regulating mechanism, disposed on the material-incoming conveyor and connected to the probe module for elevating the probe module vertically and moving the probe module horizontally; a revolving machine, connected to the material-incoming conveyor for receiving and transferring a plurality of products under measure from the material-incoming conveyor, wherein a transferring direction of the revolving machine is adjustable; and a controller, electrically connected to the material-incoming conveyor, the probe module, the probe position regulating mechanism and the revolving machine. The resistivity-measuring device achieves automatic measuring resistivity, increases the efficiency of measurement, and reduces labor power cost.

13 Claims, 9 Drawing Sheets

RESISTIVITY-MEASURING DEVICE

BACKGROUND OF THE INVENTION

This Application claims the benefit of the People's Republic of China Application No. 201210171113.9, filed on May 24, 2012.

FIELD OF THE INVENTION

The present disclosure relates to a device for measuring electrical properties, and more particularly to a resistivity-measuring device.

DESCRIPTION OF THE RELATED ART

Square resistance, also called as sheet resistance, characterizes physical quantity of film conductive performances. Resistance and resistance uniformity of films are closely related to the functions of a product. Four-probe method is usually adopted to measure resistance, the principle of which is simple and acts as a non-destructive measurement method.

The traditional measurement method includes disposing the products to be measured, such as ITO film or ITO glass on a working platform, and vertically contacting the area required to be measured of a product with the probe test head of a four-probe measurement instrument. The reading is recorded as a surface impedance of this area until the reading of the measurement instrument is stabilized.

The traditional resistivity-measuring method is completed manually with lower testing efficiency and higher labor cost. Moreover, measurement accuracy will be affected due to differences in techniques and measurement dynamics of different testers.

SUMMARY OF THE INVENTION

In view of this, this disclosure is to provide a resistivity-measuring device comprising: a carrier platform used for loading products under measure; a material-incoming conveyor, on which the carrier platform is disposed, and comprising a material-incoming guide wheel group for moving the carrier platform horizontally; a probe module is used for measuring resistances of the products under measure; a probe position regulating mechanism is disposed on the material-incoming conveyor and connected to the probe module for elevating the probe module vertically and moving the probe module horizontally; a revolving machine connects to the material-incoming conveyor and is used for receiving and transferring measured products transferred from the material-incoming conveyor, wherein a transferring direction of the revolving machine is adjustable; and a controller is electrically connected with the material-incoming conveyor, the probe module, the probe position regulating mechanism, and the revolving machine.

The present disclosure achieves the purpose of automatic measuring resistivity of products under measure, so as to improve measurement efficiency and reduce labor cost. In comparison with the known manual measurement methods, the present disclosure enhances the measurement accuracy.

BRIEF DESCRIPTION OF THE DRAWINGS

For those skilled in the art, numerous embodiments and drawings described below are for illustration purpose only, and not to limit the scope of the present disclosure in any manner.

DETAILED DESCRIPTION OF THE EMBODIMENTS

The following detailed description is made with reference to the figures. Preferred embodiments are described to illustrate the disclosure, not to limit its scope, which is defined by the claims. Those of ordinary skill in the art will recognize a number of equivalent variations in the description that follows.

Figure 1:
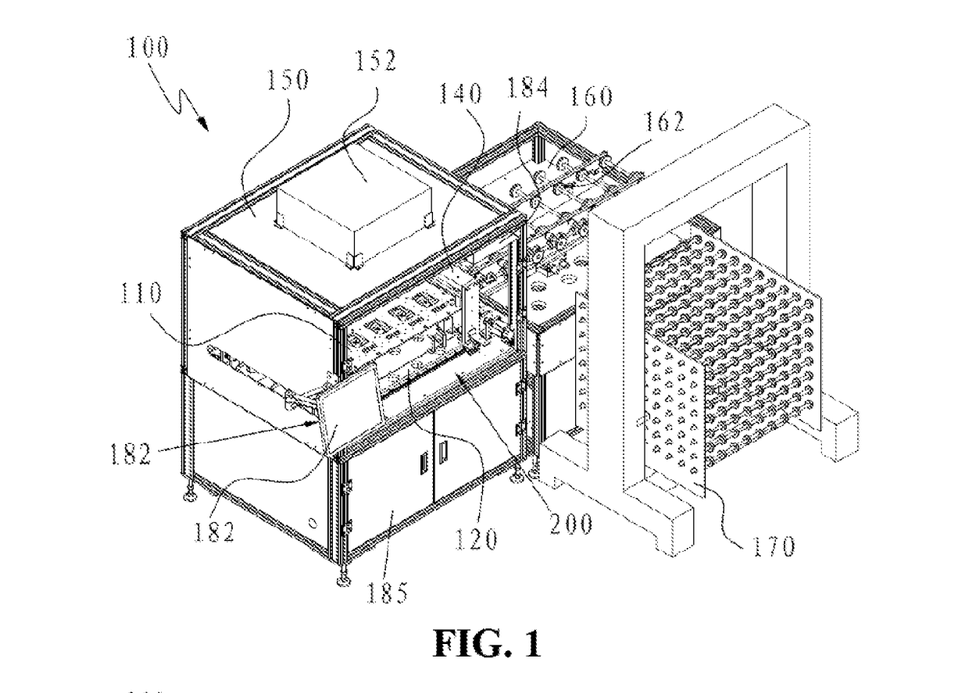
FIG. 1 illustrates a perspective diagram of an embodiment of a resistivity-measuring device according to the disclosure.
Figure 2:
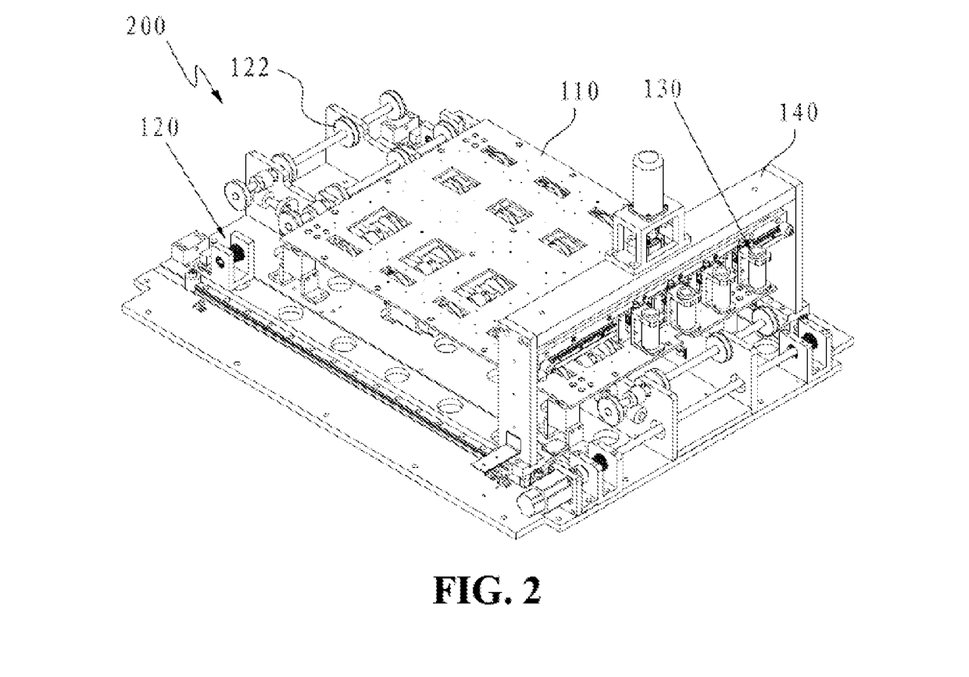
FIG. 2 illustrates a perspective diagram of the resistivity-measuring device at a probing section shown in FIG. 1.
Figure 3:
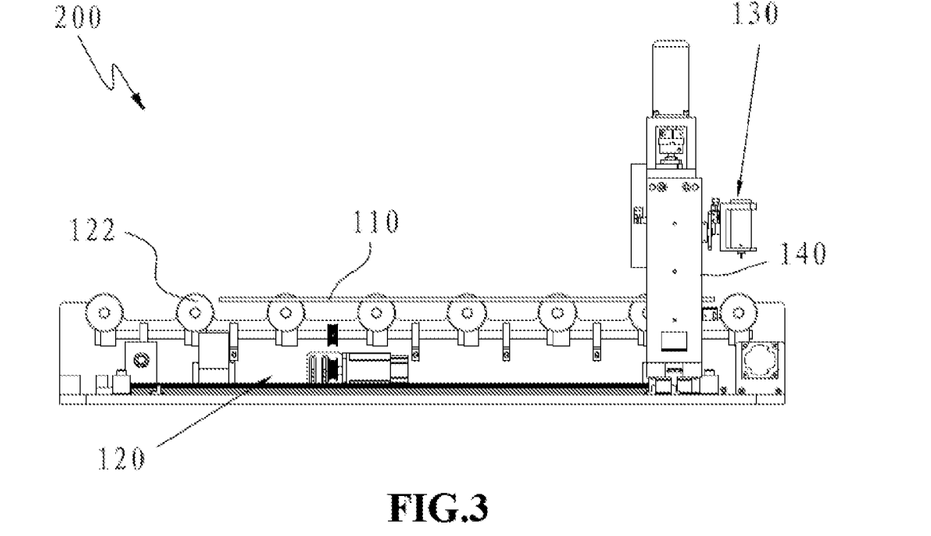
FIG. 3 illustrates a front-view diagram of the probing section shown in FIG. 2.
Figure 4:
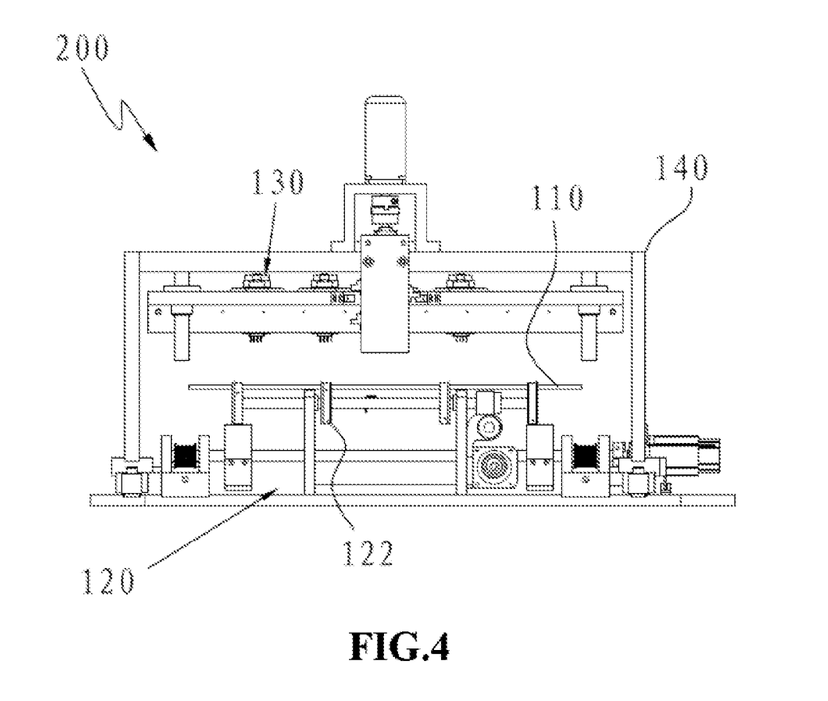
FIG. 4 illustrates a left-view diagram of the probing section shown in FIG. 2.
Figure 5:
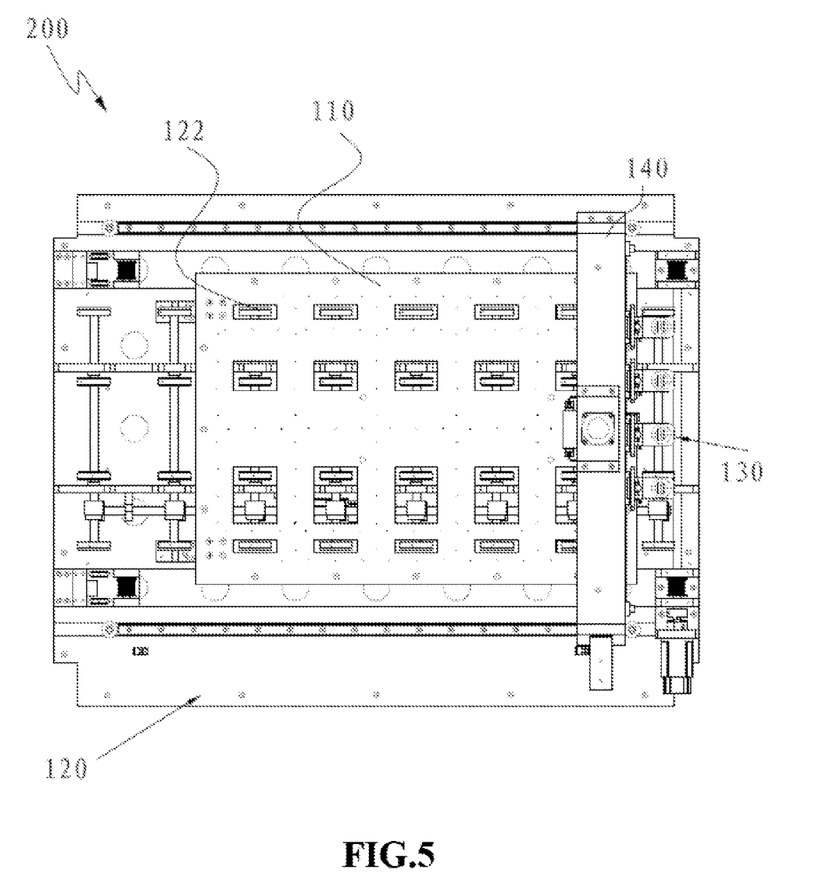
FIG. 5 illustrates a top-view diagram of the probing section shown in FIG. 2.
Figure 6:
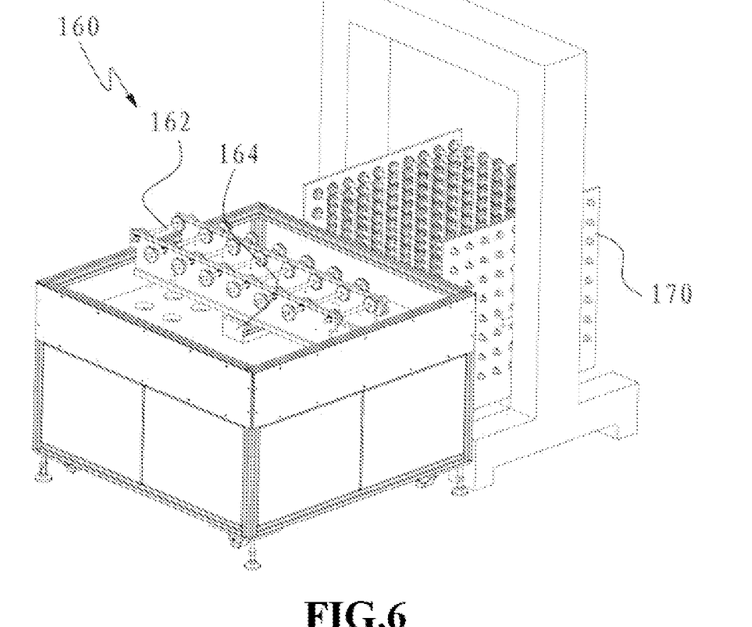
FIG. 6 illustrates a perspective diagram of a revolving machine and a material-receiving machine shown in FIG. 1.

With reference to FIGS. 1-5, FIG. 1 illustrates a perspective diagram of an embodiment of a resistivity-measuring device according to the disclosure. FIG. 2 illustrates a perspective diagram of the resistivity-measuring device 100 at the probing section 200 shown in FIG. 1. FIG. 3 illustrates a front-view diagram of the probing section 200 shown in FIG. 2. FIG. 4 illustrates a left-view diagram of the probing section 200 shown in FIG. 2. Further, FIG. 5 is a top-view diagram of the probing section 200 shown in FIG. 2. As shown in FIGS. 1-5, the resistivity-measuring device 100 comprises a carrier platform 110, a material-incoming conveyor 120, a probe module 130, a probe position regulating mechanism 140, a revolving machine 160, and a controller 183. Additionally, a probing section 200 employs the carrier platform 110, the material-incoming conveyor 120, a probe module 130, and the probe position regulating mechanism 140 together.

As shown in FIGS. 2-5, the carrier platform 110 is disposed on the material-incoming conveyor 120 for loading products under measure (not shown), such as ITO (Indium Tin Oxides) glass. The material-incoming conveyor 120 includes a material-incoming guide wheel group 122 for moving the carrier platform 110 horizontally on a plane. The probe position regulating mechanism 140 is disposed on the material-incoming conveyor 120. The probe module 130 is used for measuring resistances of the products under measure. The probe position regulating mechanism 140 connects to the probe module 130 and elevates the probe module 130 in a vertical direction, and moves the probe module 130 in a horizontal direction.

Figure 7:
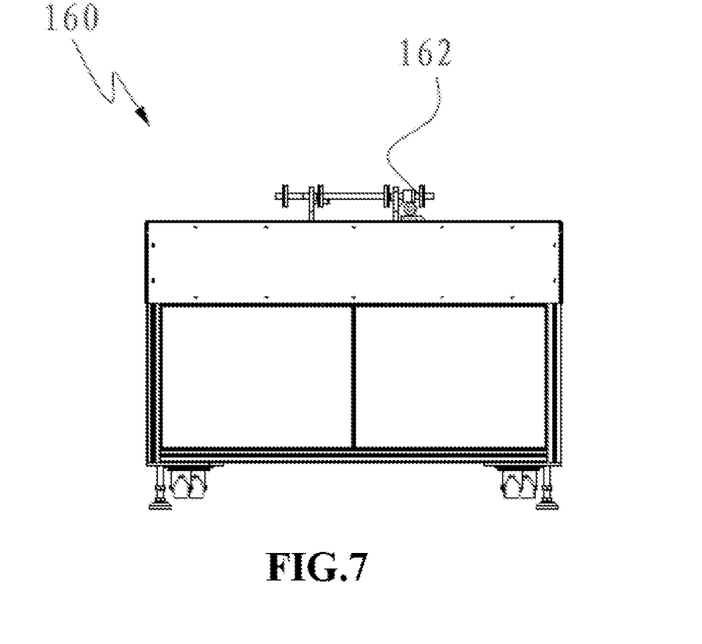
FIG. 7 illustrates a front-view diagram of the revolving machine shown in FIG. 6.
Figure 8:
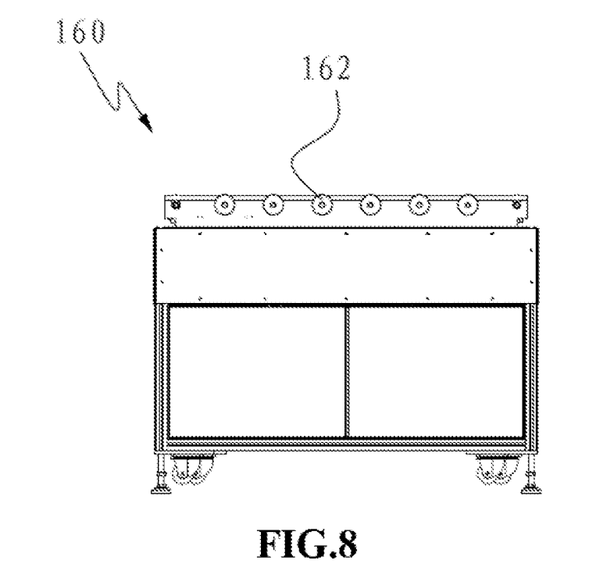
FIG. 8 illustrates left-view diagram of the revolving machine shown in FIG. 6.
Figure 9:
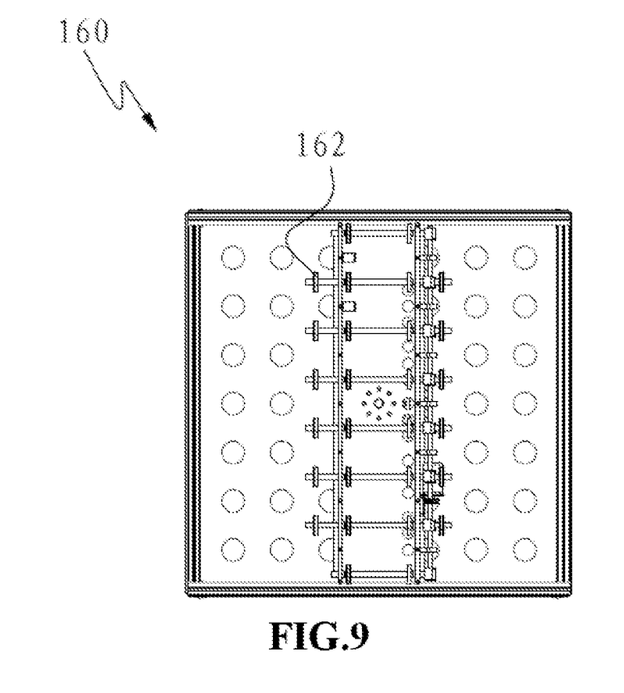
FIG. 9 illustrates a top-view diagram of the revolving machine shown in FIG. 6.

With reference to FIGS. 6-9, FIG. 6 illustrates a perspective diagram of the revolving machine 160 and the material-receiving machine 170 as shown in FIG. 1. FIG. 7 is a front-view diagram of the revolving machine 160 shown in FIG. 6. Further, FIG. 8 is a left-view diagram of the revolving machine 160 shown in FIG. 6. In addition, FIG. 9 is a top-view diagram of the revolving machine 160 shown in FIG. 6. As shown in FIGS. 6-9, one end of the revolving machine 160 is connected to the material-incoming conveyor 120 and is used for receiving and transferring a plurality of measured products transferred from the material-incoming conveyor 120, and other ends are individually connected to the material-receiving machine 170 and downstream equipment (not shown). The revolving machine 160 includes a material-discharging guide wheel group 162 that transfers the measured products from the material-incoming end of the material-discharging guide wheel group 162 to the material-discharging end of the material-discharging guide wheel group 162. The material-incoming end receives the measured products from the carrier platform 110. Moreover, the revolving machine 160 includes a revolving mechanism 164 for revolving the material-discharging guide wheel group 162 on the plane. In other words, the revolving machine 164 can revolve along a vertical axis, and the material-discharging guide wheel group 162 can be driven toward different directions. The revolving mechanism 164 controls the material-discharging guide wheel group 162 for transferring the measured products to the material-receiving machine 170 or downstream equipment.

The controller 183 is electrically connected with the material-incoming conveyor 120, the probe module 130, the probe position regulating mechanism 140 and the revolving machine 160, so as to control the rotation of the material-incoming guide wheel group 122 to move the products under measure horizontally from the carrier platform 110 to the underneath side of the probe module 130. The controller 183 subsequently controls the probe position regulating mechanism 140 to press the probe module 130 for forming ohm connection with the surface of the products under measure to conduct resistance measurement. According to the types of the products under measure, the probe module 130 is vertically moved to adjust the contact position between the probe module 130 and the products under measure. On completion of the resistance measurement, the controller 183 subsequently regulates the carrier platform 110 descending and the probe module 130 ascending to separate the probe module 130 and the measured products.

In addition, the controller 183 simultaneously operates material-incoming conveyor 120 and the revolving machine 160 to transfer the measured products to the revolving machine 160 through the material-discharging guide wheel group 162. Moreover, during this controlled operation, the measured products are transferred to the downstream equipment or the material-receiving machine 170 according to the result of previous resistance measurement. If the result is passed, the material-discharging guide wheel group 162 may transfer the measured products to the downstream equipment for conducting the subsequent process flows, such as cleaning and screen-printing. On the other hand, if the result is unqualified, the controller 183 operates the revolving mechanism 164 to revolve the material-discharging guide wheel group 162 horizontally by 90 degrees, so that the measured products are transferred into the material-receiving machine 170.

In other embodiments, the positions of the material-receiving machine 170 and the downstream equipment are exchanged. Further, the material-receiving machine 170 may be replaced with other equipments that can accept the measured products with unqualified resistance measurement, and the controller 183 can use the programmable logic controller 183 of Omron.

The resistivity-measuring device 100 achieves the purpose of automatic measuring resistivity and improves measurement efficiency and accuracy as compared to manual measurement and reduces labor power cost. The products with unqualified measurement may be automatically transferred into the material-receiving machine 170 through the revolving machine 160, preventing detective products with unqualified resistance values from flowing out Referring to FIG. 1, in one embodiment, the resistivity-measuring device 100 may include a dust-proof cover 150 within which the probing section 200 is set. An air filter 152 is set on the dust-proof cover 150 to avoid the accumulation of dusts within the dust-proof cover 150. In an alternate embodiment, the carrier platform 110 can be a sucker platform. Further, the material-incoming guide wheel group 122 employs the magnetic guide wheel group to achieve the non-contact transmission, efficiently reducing the generation of dust.

Figure 10:
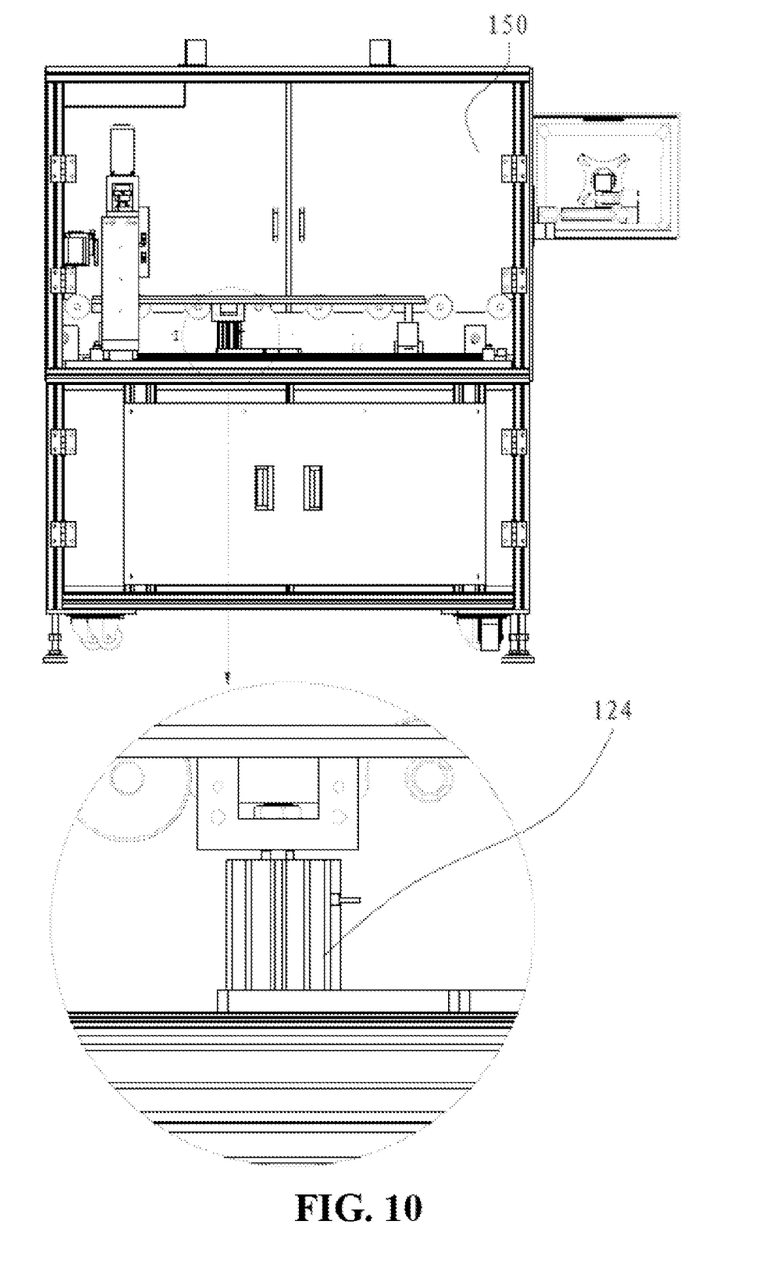
FIG. 10 illustrates a schematic diagram of an elevator mechanism of the resistivity-measuring device shown in FIG. 1.

FIG. 10 illustrates a schematic diagram of an elevator mechanism of the resistivity-measuring device shown in FIG. 1. The resistivity-measuring device 100 includes an elevator mechanism 124 for elevating the carrier platform 110. In one embodiment, the elevator mechanism 124 can be driven by an air cylinder (not shown).

As shown in FIGS. 1 and 2, the resistivity-measuring device 100 further includes host machine 185, a displayer 182, and a digital source meter 184. The host machine 185 is electrically connected to the displayer 182. Further, the host machine 185 includes a digital input & output card (not shown), and the host machine 185 electrically connects with the digital source meter 184 and the probe module 130 through the digital input & output card. The host machine 185 can provide additional operating instructions to the digital source meter 184 or the probe module 130 and receives feedback messages from the digital source meter 184 or the probe module 130. The host machine 185 can be placed beneath the dust-proof cover 150. In one embodiment, the digital source meter 184 employs Keithley 2400c, and the digital input & output card employs PCI-7230. Moreover, the host machine installed with resistivity-measuring software can conduct resistivity measurement.

Figure 11:
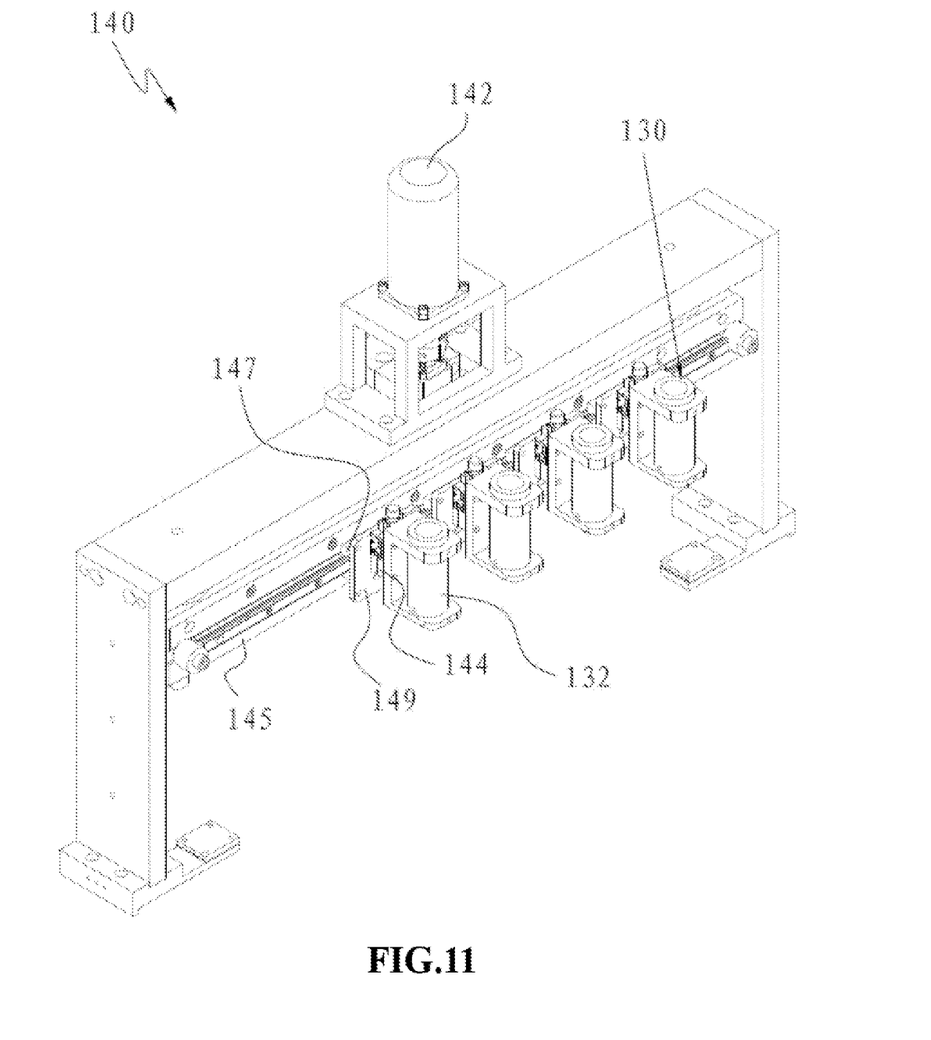
FIG. 11 illustrates a perspective diagram of a probe position regulating mechanism and a probe module according to the disclosure.
Figure 12:
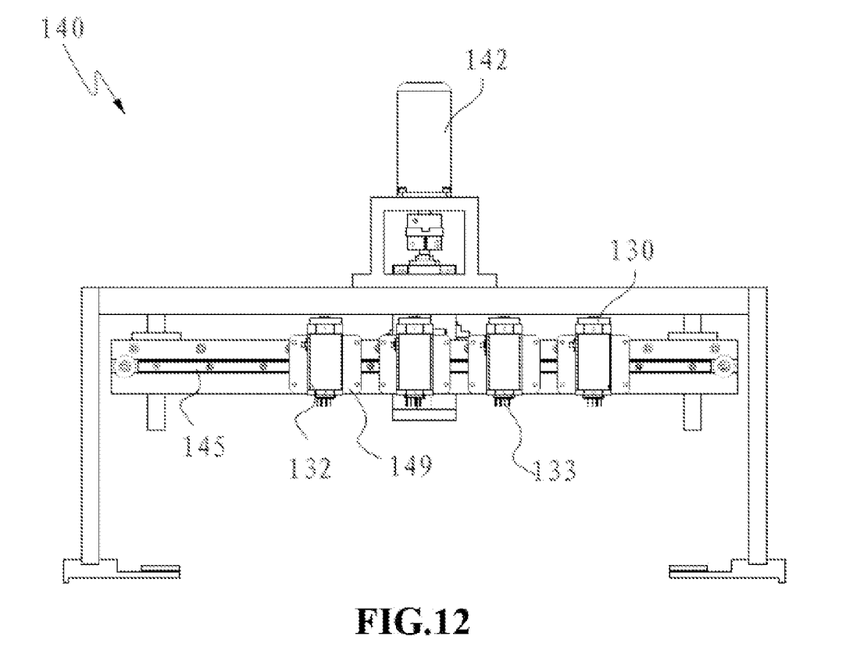
FIG. 12 illustrates a front-view diagram of the probe position regulating mechanism and the probe module shown in FIG. 11.

FIG. 11 illustrates a perspective diagram of the probe position regulating mechanism 140 and a probe module 130 according to the disclosure. In addition, FIG. 12 is a front-view diagram of the probe position regulating mechanism 140 and the probe module 130 shown in FIG. 11. In the embodiment, the probe module 130 includes four probe measuring heads 132 arranged at equal distances. In other embodiment, the probe measuring heads 132 can be arranged at unequal distances, but the same is not limited herein. In one implementation, each probe measuring head 132 may include four circular probes 133 arranged in turns. On measuring resistance, the main machine controls the digital input & output card to switch the electricity-conduction and electricity-interruption of four probe measuring heads 132 in turns. The main machine provides low current (as 4.532 mA in one embodiment) to the first and fourth probes of the probe measuring head 132 via the digital source meter 184. The voltage between the second and third probes of the probe measuring head 132 is measured, followed by sheet resistance and resistance uniformity determination of the measured product using the corresponding formulae. The data related to the sheet resistance and resistance uniformity is automatically collected and reserved through the main machine, identifying whether the measured product is qualified or not, depending on the pre-determined upper and lower limit threshold values. The displayer 182 can show the measured data and qualification status.

In certain embodiments, the resistivity-measuring device 100 can be set according to the type of the product under measure, the measuring position on the product under measure, and the proposal for manufacture process. In addition, the quantity of the probe measuring heads 132 employed by the probe module 130, the number of circular measurement, and the quantity of points measured may be regulated. In one example, the quantity of probe measuring heads 132 can be 3 or 4, and the number of circular measurement may be 3 or 4 times, and the quantity of measured points can be 9, 12 or 16 points.

Figure 13:
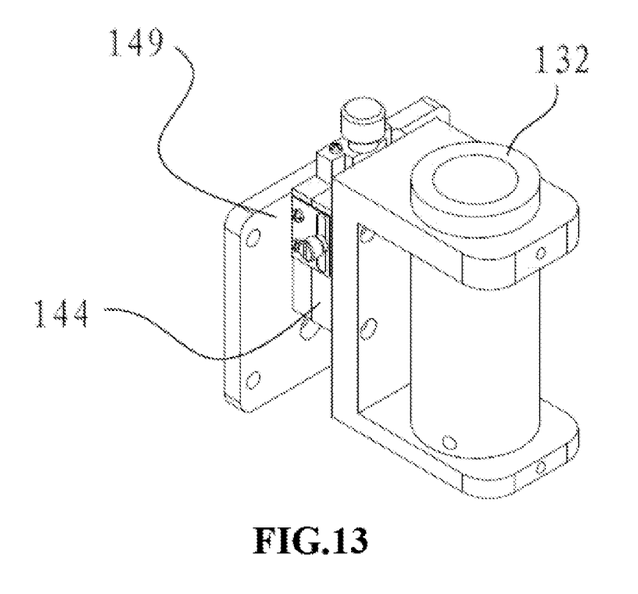
FIG. 13 illustrates a perspective diagram of combination of one probe measuring head, one sliding table and one adapter plate.
Figure 14:
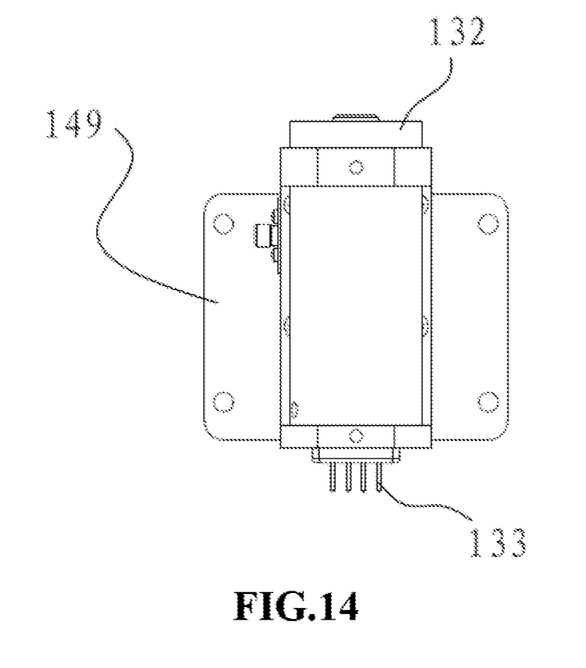
FIG. 14 illustrates a front-view diagram of combination of one probe measuring head, one sliding table and one adapter plate shown in FIG. 13.
Figure 15:
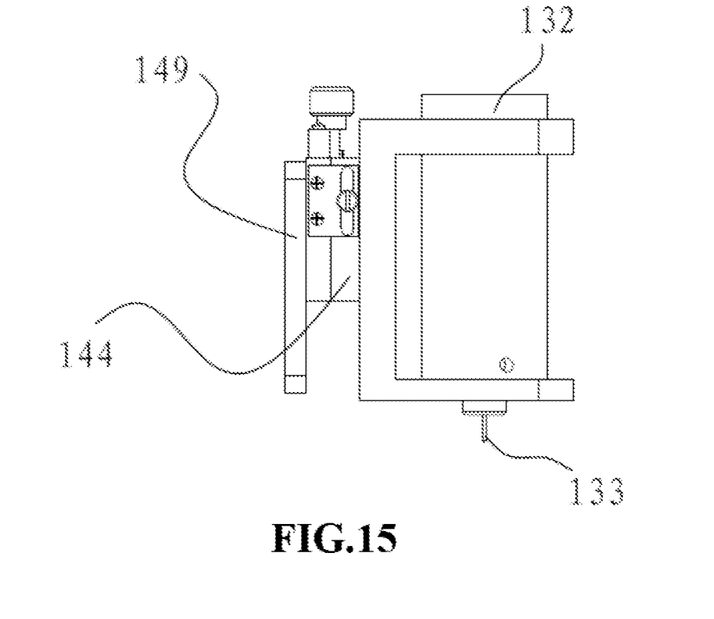
FIG. 15 illustrates a left-view diagram of combination of one probe measuring head, one sliding table and one adapter plate shown in FIG. 13.

FIG. 13 illustrates a perspective diagram of combination of one probe measuring head 132, one sliding table 144 and one adapter plate 149. Further, FIG. 14 illustrates a front-view diagram of combination of one probe measuring head 132, one sliding table 144 and one adapter plate 149 shown in FIG. 13. Additionally, FIG. 15 illustrates a left-view diagram of combination of one probe measuring head 132, one sliding table 144 and one adapter plate 149 shown in FIG. 13. As shown in FIGS. 11-15, the probe position regulating mechanism 140 includes Z-axis servo motor 142 for elevating the probe module 130. The probe position regulating mechanism 140 further includes a guide track 145, a sliding block 147, an adapter plate 149, and a sliding table 144. Each probe measuring head 132 of the probe module 130 is set on the sliding table 144 that is jointed fixedly to the sliding block 147 through the adapter plate 149. The sliding block 147 is jointed to the guide track 145 while sliding on it, which can drive the probe measuring head 132 to slide on the guide track 145. Moreover, the pushing distance of Z-axis servo motor can be adjusted according to the thickness of the product under measure. The probe measuring heads 132 may be adjusted to the same height by regulating the sliding table 144.

Please refer to FIGS. 2 and 6 again, the resistivity-measuring device 100 may further include a plurality of guide rods. Further, the material-incoming guide wheel group 122 and the material-discharging guide wheel group 162 may be set on and driven by these guide rods.

Through actual estimation, the precision for an ITO-coated glass plane measured by the foregoing resistivity-measuring device 100 can reach within ±0.1Ω, meanwhile, the time of measurement is reduced from the previous 60 sec to the present 20~35 sec. In addition, the resistivity-measuring device 100 can operate to measure without manual operation.

While certain embodiments have been shown and described, various modifications and substitutions may be made thereto without departing from the spirit and scope of the disclosure. Therefore, it is to be understood that the present disclosure has been described by way of illustration and not limitations.

What is claimed is:

1. A resistivity-measuring device, comprising: a carrier platform used for loading a plurality of products under measure; a material-incoming conveyor, on which the carrier platform is disposed, and the material-incoming conveyor comprises a material-incoming guide wheel group for moving the carrier platform horizontally; a probe module comprising a plurality of probe measuring heads, used for measuring the resistance of the products under measure; a probe position regulating mechanism, disposed on the material-incoming conveyor and connected to the probe module for elevating the probe module vertically and moving the probe module horizontally; a revolving machine, connected to the material-incoming conveyor for receiving and transferring a plurality of products under measure from the material-incoming conveyor, wherein a transferring direction of the revolving machine is adjustable; and a controller, electrically connected to the material-incoming conveyor, the probe module, the probe position regulating mechanism, and the revolving machine; and wherein the probe position regulating mechanism comprises a guide track, a sliding block, an adapter plate and a sliding platform, wherein the probe measuring heads are set on the sliding platform, the sliding platform is fixed to the sliding block through the adapter plate, and the sliding block is jointed to the guide track.

2. The resistivity-measuring device of claim 1, wherein the revolving machine comprises a material-discharging guide wheel group for transferring the measured products and a revolving mechanism for revolving the material-discharging guide wheel group.

3. The resistivity-measuring device of claim 1, further comprising a material-receiving machine connected to the revolving machine.

4. The resistivity-measuring device of claim 1, wherein the carrier platform is a sucker platform, and the material-incoming guide wheel group is a magnetic guide wheel group.

5. The resistivity-measuring device of claim 1, further comprising a host machine, a displayer, and a digital source meter.

6. The resistivity-measuring device of claim 5, wherein the host machine is electrically connected to the displayer, the digital source meter, and the probe module.

7. The resistivity-measuring device of claim 5, wherein the host machine comprises a digital input & output card, electrically connected to the digital source meter and the probe module.

8. The resistivity-measuring device of claim 1, further comprising a dust-proof cover, wherein the carrier platform, the material-incoming conveyor, the probe module, and the probe position regulating mechanism are disposed in the dust-proof cover.

9. The resistivity-measuring device of claim 8, further comprising an air filter set on the dust-proof cover to avoid the accumulation of dust within the dust-proof cover.

10. The resistivity-measuring device of claim 1, further comprising an elevating mechanism for elevating the carrier platform.

11. The resistivity-measuring device of claim 10, wherein the elevating mechanism is driven by an air cylinder.

12. The resistivity-measuring device of claim 1, wherein each of the probe measuring heads comprises a plurality of circular probes.

13. The resistivity-measuring device of claim 1, wherein the probe position regulating mechanism comprises a Z-axis servo motor for elevating the probe module.

* * * * *